United States Patent
Vukos et al.

(10) Patent No.: US 6,969,378 B1
(45) Date of Patent: Nov. 29, 2005

(54) BIAXIAL STRETCH GARMENT

(75) Inventors: John Philip Vukos, Neenah, WI (US); Georgia Lynn Zehner, Larsen, WI (US); Duane Girard Uitenbroek, Little Chute, WI (US); Richard Warren Tanzer, Neenah, WI (US); Nancy E. Dawson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 686 days.

(21) Appl. No.: 09/698,517

(22) Filed: Oct. 27, 2000

(51) Int. Cl.[7] ............................................. A61F 13/15
(52) U.S. Cl. ........................ 604/385.22; 604/385.01; 604/385.16; 604/385.25; 604/385.3; 604/378
(58) Field of Search ...................... 604/385.01, 385.16, 604/385.22, 385.23, 378, 385.25, 385.3

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,443,513 A | 4/1984 | Meitner et al. | |
| 4,543,099 A | 9/1985 | Bunnelle et al. | |
| 4,606,964 A | 8/1986 | Wideman | |
| 4,640,726 A | 2/1987 | Sallee et al. | |
| 4,704,116 A | 11/1987 | Enloe | |
| 4,720,415 A | 1/1988 | Vander Wielen et al. | |
| 4,756,709 A | 7/1988 | Stevens | |
| 4,801,485 A | 1/1989 | Sallee et al. | |
| 4,810,556 A | 3/1989 | Kobayashi et al. | |
| 4,829,096 A | 5/1989 | Kitamura et al. | |
| 4,863,779 A | 9/1989 | Daponte | |
| 4,908,247 A | 3/1990 | Baird et al. | |
| 4,938,757 A | 7/1990 | Van Gompel et al. | |
| 4,965,122 A | 10/1990 | Morman | |
| 4,981,747 A | 1/1991 | Morman | |
| 5,036,551 A | 8/1991 | Dailey et al. | |
| 5,114,781 A | 5/1992 | Morman | |
| 5,116,662 A | 5/1992 | Morman | |
| 5,143,679 A | 9/1992 | Weber et al. | |
| 5,149,741 A | 9/1992 | Alper et al. | |
| 5,156,793 A | 10/1992 | Buell et al. | |
| 5,167,897 A | 12/1992 | Weber et al. | |
| 5,171,239 A | 12/1992 | Igaue et al. | |
| 5,171,388 A | 12/1992 | Hoffman et al. | |
| 5,244,482 A | 9/1993 | Hassenboehler, Jr. et al. | |

(Continued)

FOREIGN PATENT DOCUMENTS

EP        321 985        6/1989

(Continued)

*Primary Examiner*—Larry I. Schwartz
*Assistant Examiner*—Jacqueline F. Stephens
(74) *Attorney, Agent, or Firm*—Pauley Petersen & Erickson

(57) ABSTRACT

A biaxial stretch, form-fitting, pant-like, absorbent garment has a stretchable outer cover, a stretchable body side liner, and a stretchable absorbent assembly. The outer cover and the body side liner are desirably biaxially stretchable. The absorbent assembly can either be biaxially stretchable or segmented with longitudinal stretch. The absorbent garment is easy to apply, has a self-adjusting feature, and delivers enhanced fit and comfort during use without restricting a wearer's movement.

18 Claims, 5 Drawing Sheets

U.S. PATENT DOCUMENTS

| | | |
|---|---|---|
| 5,259,902 A | 11/1993 | Muckenfuhs |
| 5,336,545 A | 8/1994 | Morman |
| 5,354,400 A | 10/1994 | Lavash et al. |
| 5,385,775 A | 1/1995 | Wright |
| 5,397,316 A | 3/1995 | LaVon et al. |
| 5,492,753 A | 2/1996 | Levy et al. |
| 5,496,429 A | 3/1996 | Hasse et al. |
| 5,514,470 A | 5/1996 | Haffner et al. |
| 5,527,302 A | 6/1996 | Endres et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,556,504 A | 9/1996 | Rajala et al. |
| 5,560,878 A | 10/1996 | Dragoo et al. |
| 5,569,232 A | 10/1996 | Roe et al. |
| 5,569,234 A | 10/1996 | Buell et al. |
| 5,582,903 A | 12/1996 | Levy et al. |
| 5,587,225 A | 12/1996 | Griesbach et al. |
| 5,611,790 A | 3/1997 | Osborn, III et al. |
| 5,615,460 A | 4/1997 | Weirich et al. |
| 5,624,422 A | 4/1997 | Allen |
| 5,624,427 A | 4/1997 | Bergman et al. |
| 5,624,729 A | 4/1997 | Cohen et al. |
| 5,628,741 A | 5/1997 | Buell et al. |
| 5,628,856 A | 5/1997 | Dobrin et al. |
| 5,635,290 A | 6/1997 | Stopper et al. |
| 5,643,396 A | 7/1997 | Rajala et al. |
| 5,645,672 A | 7/1997 | Dobrin |
| 5,658,269 A | 8/1997 | Osborn, III et al. |
| 5,660,657 A | 8/1997 | Rajala et al. |
| 5,674,212 A | 10/1997 | Osborn, III et al. |
| 5,683,375 A | 11/1997 | Osborn, III et al. |
| 5,690,627 A | 11/1997 | Clear et al. |
| 5,702,382 A | 12/1997 | Osborn, III et al. |
| 5,713,884 A | 2/1998 | Osborn, III et al. |
| 5,716,478 A | 2/1998 | Boothe et al. |
| 5,749,866 A | 5/1998 | Roe et al. |
| 5,749,989 A | 5/1998 | Linman et al. |
| 5,759,340 A | 6/1998 | Boothe et al. |
| H1750 H | 9/1998 | Dobrin |
| 5,843,056 A | 12/1998 | Good et al. |
| 5,883,028 A | 3/1999 | Morman et al. |
| 5,942,569 A | 8/1999 | Simmons et al. |
| 5,964,743 A * | 10/1999 | Abuto et al. ............ 604/385.01 |
| 6,004,306 A | 12/1999 | Robles et al. |
| 6,129,720 A | 10/2000 | Blenke et al. |

FOREIGN PATENT DOCUMENTS

| | | | |
|---|---|---|---|
| EP | 0 236 032 | 12/1991 | |
| EP | 0 386 816 | 4/1994 | |
| EP | 591 647 | 4/1994 | |
| EP | 0 400 111 | 8/1994 | |
| EP | 0 451 705 | 8/1994 | |
| EP | 0 630 630 | 12/1994 | |
| EP | 0 630 631 | 12/1994 | |
| EP | 0 630 632 | 12/1994 | |
| EP | 630 632 | 12/1994 | |
| EP | 0 420 256 | 5/1995 | |
| EP | 0 707 106 | 4/1996 | |
| EP | 0 433 951 | 8/1996 | |
| EP | 0 552 345 | 9/1996 | |
| EP | 0 630 221 | 4/1997 | |
| EP | 0 409 315 | 5/1997 | |
| EP | 0 820 747 | 1/1998 | |
| EP | 0 602 613 | 6/1998 | |
| EP | 0 651 629 | 6/1998 | |
| EP | 0 659 117 | 6/1998 | |
| WO | 93/01785 | 2/1993 | |
| WO | 93/17648 | 9/1993 | |
| WO | 94/02094 | 2/1994 | |
| WO | 95/07063 | 3/1995 | |
| WO | 96/16625 | 6/1996 | |
| WO | 96/18367 | 6/1996 | |
| WO | 97/21410 | 6/1997 | |
| WO | 97/36566 | 10/1997 | |
| WO | 98/55065 | 12/1998 | |
| WO | 99/00095 | 1/1999 | |
| WO | WO 9933426 A1 * | 7/1999 | ........... A61F 13/15 |
| WO | 99/59514 | 11/1999 | |
| WO | 00/30582 | 6/2000 | |

* cited by examiner

BIAXIAL STRETCH GARMENT

FIELD OF THE INVENTION

This invention is directed to a diaper that is able to stretch in multiple directions. More particularly, all of the components of the diaper have the ability to extend, thereby not restricting a wearer's movements.

BACKGROUND OF THE INVENTION

Pant-like absorbent garments, such as adult incontinence wear, infant and children's diapers, swim wear and training pants, typically have some degree of stretchability in order to conform to a wearer's body. Present diapers, for example, have stretchable side panels with non-stretchable outer covers, bodyside liners and absorbent assemblies. When this type of diaper is worn, only the side panels stretch.

Different portions of a diaper have different stresses imposed by the size and movements of the infant. Some conventional diapers do not allow these stresses to be relieved except by degradation of fit, and where the stresses are not relieved by fit degradation, discomfort and redmarking of skin can result. When fit is degraded, leakage protection provided by the diaper is also degraded. When such conventional diapers degrade with wear time, the side panels narrow, concentrating force along the sides at the fastening region of the diaper. The high force load on the fastening region often leads to fastener failure or red marking and discomfort.

Some conventional diapers are difficult to apply as a result of their inability to adapt to the differences in infant shapes. Further difficulty may be encountered by a conventional diaper's tendency to fold back on itself or curl up before application to an infant. Furthermore, many conventional diapers do not hold the target area portions of the liner and absorbent close to the body, thus giving bodily wastes time to spread across the skin before being absorbed by the diaper.

There is a need or desire for form-fitting, pant-like, personal care absorbent garments that disperse forces in the side panels to prevent narrowing of the side panels.

There is a further need or desire for form-fitting, pant-like, personal care absorbent garments that conform to a wearer's body without restricting the wearer's movement.

There is yet another need or desire for form-fitting, pant-like, personal care absorbent garments that are easy to apply to a wearer's body.

There is still another need or desire for form-fitting, pant-like, personal care absorbent garments that are adapted to fit a wide range of sizes.

There is a further need or desire for form-fitting, pant-like, personal care absorbent garments that intercept bodily wastes before the waste has an opportunity to spread on the skin.

SUMMARY OF THE INVENTION

The present invention is directed to biaxial stretch, pant-like absorbent garments that are easy to apply, have a self-adjusting feature, and deliver enhanced fit and comfort during use. More particularly, the absorbent garment of the present invention utilizes biaxial stretch materials to deliver all-direction stretch throughout the garment chassis. The biaxial stretch materials also enable the garment to equalize tensions in any direction, in any part of the garment. In order for the garment to be able to stretch in all directions, all of the components of the garment must be able to extend and not restrict movement.

The biaxial stretch, pant-like absorbent garments of the present invention have a stretchable chassis, including a stretchable outer cover, a stretchable body side liner, and a stretchable absorbent assembly between the outer cover and the body side liner. The stretchable materials can either be extensible and retractable or extensible and non-retractable. Stretchable side panels can either be extensions of the stretchable assembly, or can be bonded to the stretchable assembly. Either way, dispersion of forces in the side panels eliminates the narrowing of the side panels that may occur in conventional diapers. Furthermore, this dispersion of forces in the fastener region results in less negative effect on the fastener system compared to conventional diapers.

The biaxial stretch throughout the garment also provides improved comfort by allowing enhanced conformance to the wearer and allowing the wearer to move without restricting movement. The design also can allow elimination of added pieces of elastic as used in conventional absorbent garment designs by having the elastic integral with the major components of the garment.

A biaxial stretch absorbent garment, such as a biaxial stretch diaper, in accordance with the present invention, is much easier to apply than conventional diapers because of the ability of the biaxial stretch diaper to stretch and adapt to the particular shape of the wearer. The present invention is also easier to apply as a result of the majority of the elastic forces in the biaxial stretch diaper being non-retracted in the un-applied state. This allows the biaxial stretch diaper to remain flat while the care giver is beginning to apply the biaxial stretch diaper to the wearer.

The present invention can fit a wide size range of wearers because of the ability of the biaxial stretch absorbent garment to extend in all directions, and in particular the ability to extend in the longitudinal direction gives greater adjustability for the rise dimension of the wearer. The present invention has the ability to "self-adjust" as a result of the dispersion of forces around the garment. Slightly off-center application by the care giver is corrected by the garment moving to disperse unequal forces. The garment functions more efficiently than many conventional diapers as a result of the elastic forces of the components holding the absorbent and liner closer to the wearer's body. This results in interception of bodily wastes before the waste has an opportunity to spread on the skin.

With the foregoing in mind, it is a feature and advantage of the present invention to provide biaxial stretch, form-fitting, pant-like, absorbent garments that are easy to apply, have a self-adjusting feature, and deliver enhanced fit and comfort during use.

DEFINITIONS

Within the context of this specification, each term or phrase below will include the following meaning or meanings.

"Biaxial stretch" refers to a material having stretchability in two directions perpendicular to one another, e.g. stretchability in a machine direction and in a cross direction, or in a longitudinal direction (front to back) and a lateral direction (side to side)..

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Elastic,""elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 2:
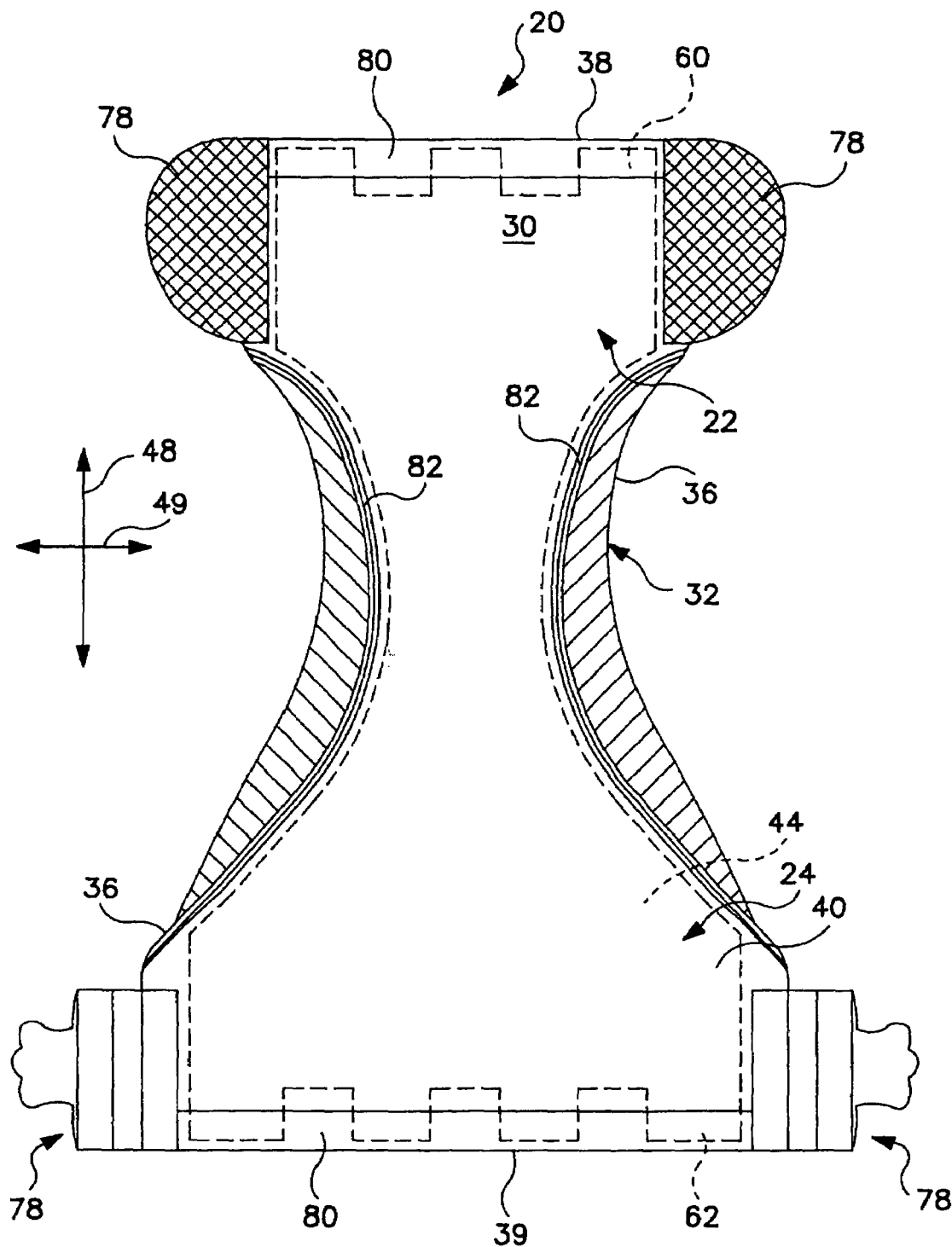
FIG. 2 is a plan view of the absorbent garment of FIG. 1 in a stretched flat state, and showing the surface of the article that faces away from the wearer when the article is worn.
Figure 3:
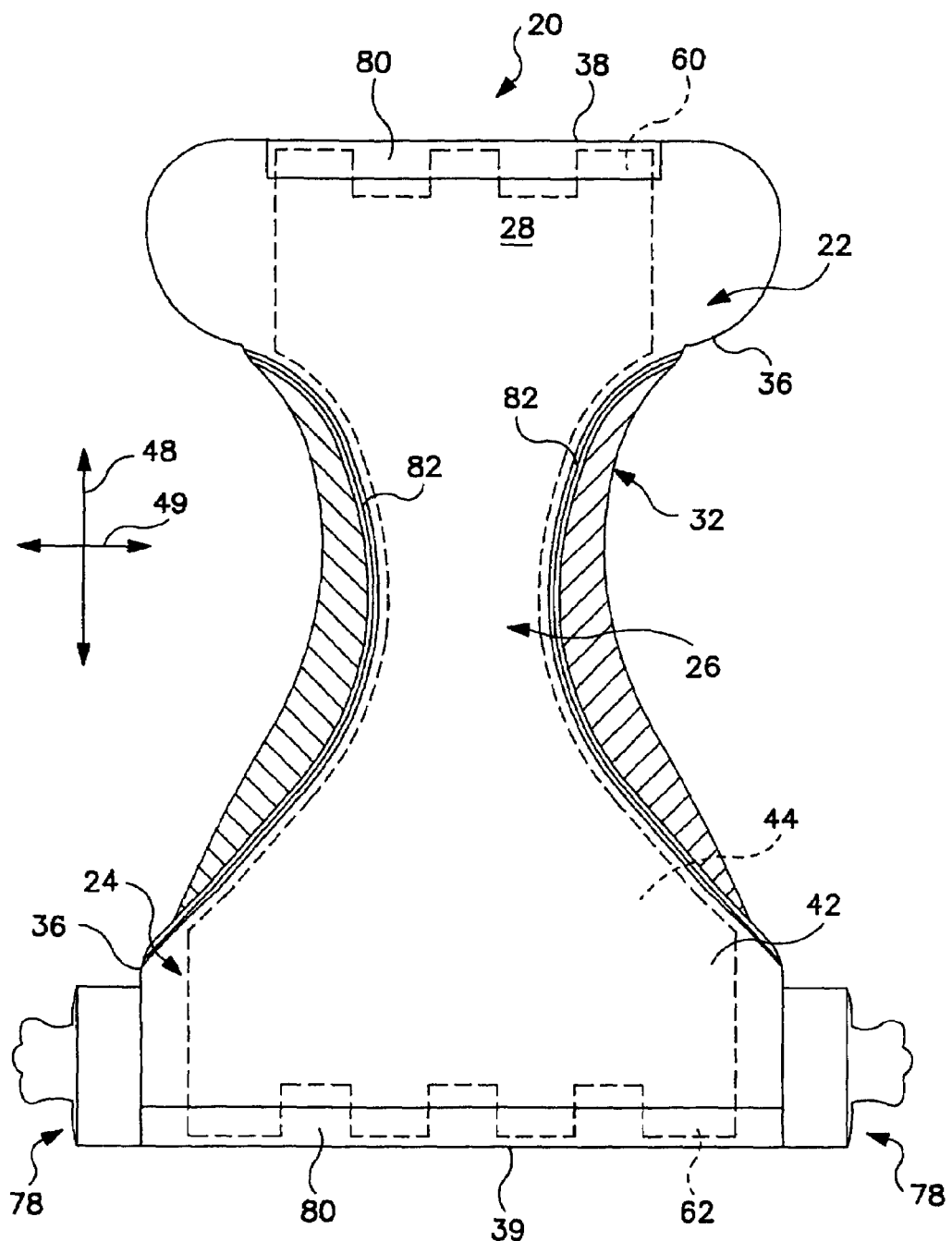
FIG. 3 is a plan view of the absorbent garment of FIGS. 1 and 2 in a stretched flat state, and showing the surface of the article that faces the wearer when the article is worn.
Figure 4:
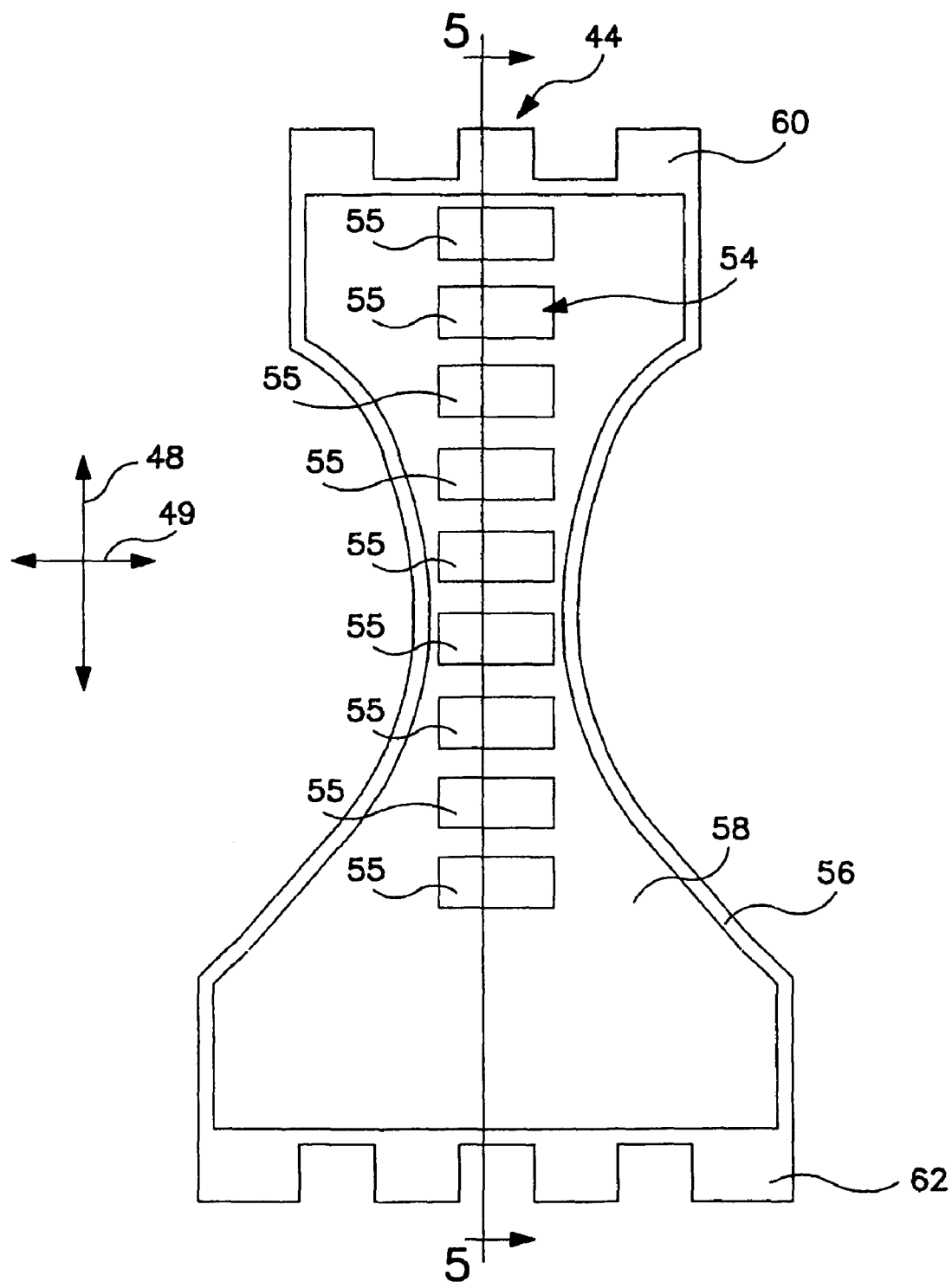
FIG. 4 is a plan view of an absorbent assembly suitable for use in the absorbent garment of FIGS. 1–3.

"Longitudinal" and "transverse" have their customary meaning, as indicated by the longitudinal and transverse axes depicted in FIGS. 2–4. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Longitudinal stretch" refers to stretchability in the longitudinal direction along the longitudinal axis.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 decitex, and are generally self bonding when deposited onto a collecting surface. Meltblown fibers used in the present invention are preferably substantially continuous in length.

"Microfibers" are small diameter fibers typically having an average fiber denier of about 0.005–10. Fiber denier is defined as grams per 9000 meters of a fiber. For a fiber having circular cross-section, denier may be calculated as fiber diameter in microns squared, multiplied by the density in grams/cc, multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 calculated as ($15^2 \times 0.89 \times 0.00707 =$ 1.415). Outside the United States the unit of measurement is more commonly the "tex," which is defined as the grams per kilometer of fiber. Tex may be calculated as denier/9. A decitex is 0.1 of a tex.

"Necked" or "neck-stretched" interchangeably refer to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. Nos. 4,443,513 to Meitner and Notheis, 4,965,122, 4,981,747 and 5,114,781 to Morman and 5,244,482 to Hassenboehler Jr. et al.

"Nonwoven" and "nonwoven web" refer to fibrous materials and webs of fibrous material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pats. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often are larger than about 0.3 decitex, more particularly, between about 0.6 and 10 decitex.

"Stretchable" or "extensible" means that a material can be stretched, without breaking, by at least 50% (to at least 150% of its initial (unstretched) length) in at least one direction, suitably by at least 100% (to at least 200% of its initial length), desirably by at least 150% (to at least 250% of its initial length). The term includes elastic materials as well as materials that stretch but do not significantly retract.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a polymer material that softens and flows when exposed to sufficient heat and which substantially returns to a nonsoftened condition when cooled to room temperature.

These terms may be defined with additional language in the remaining portions of the specification.

DETAILED DESCRIPTION OF THE PRESENTLY PREFERRED EMBODIMENTS

The present invention is directed to a biaxial stretch, form-fitting, pant-like, absorbent garment having a stretchable/extensible outer cover, a stretchable/extensible body side liner, and a stretchable/extensible absorbent assembly.

The principles of the present invention can be incorporated into any suitable disposable, pant-like, absorbent article. Examples of such suitable articles include diapers, training pants, incontinence products, swim wear, other personal care or health care garments, or the like. For ease of explanation, the description hereafter will be in terms of a diaper.

Figure 1:
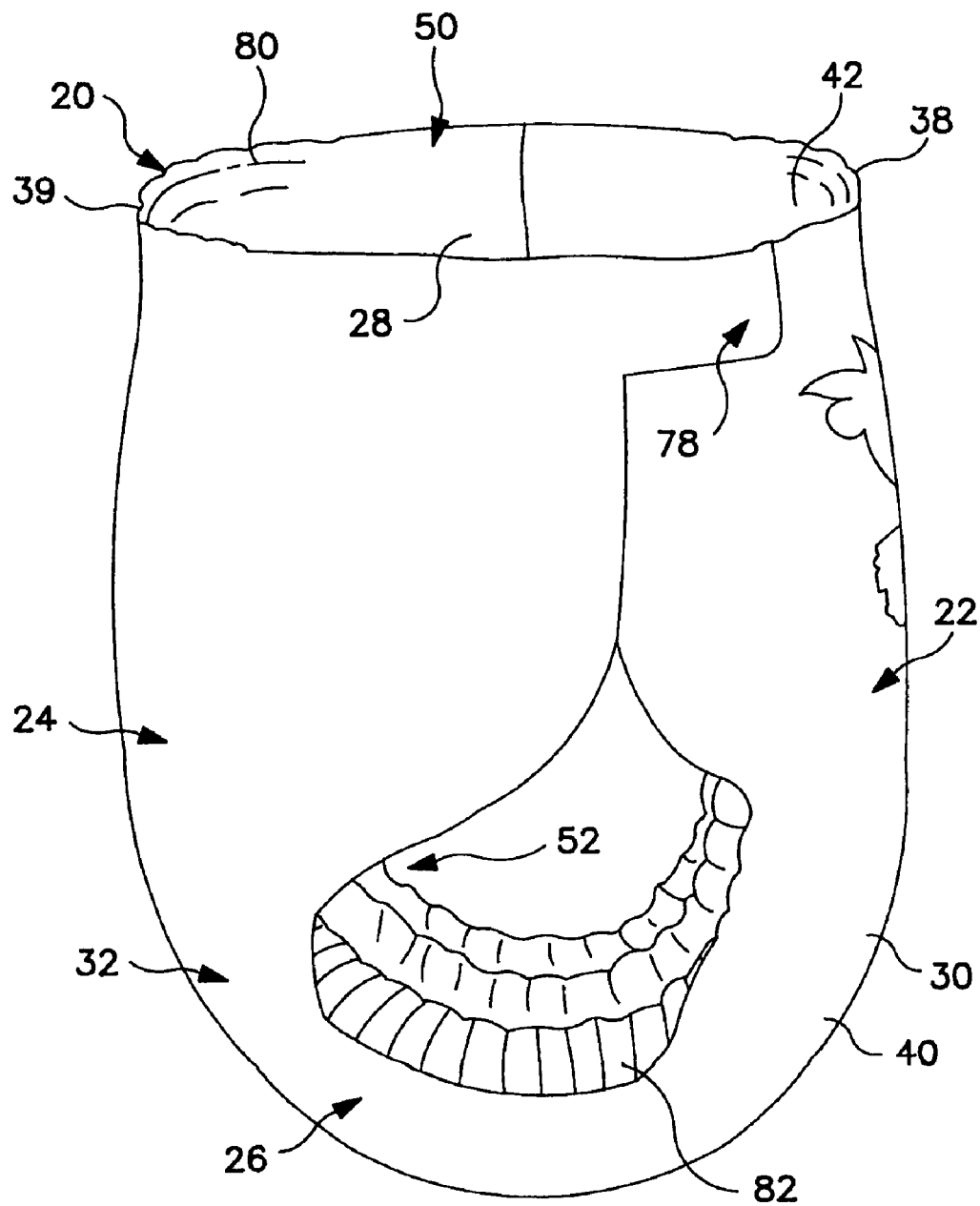
FIG. 1 is a side perspective view of a biaxial stretch absorbent garment in a fastened position.

Referring to FIGS. 1 and 2, a disposable absorbent article, such as a diaper 20, is illustrated. The diaper 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. Referring to FIG. 2, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

As shown in the diaper 20 in FIG. 1, the crotch region 26 and front and back regions 22 and 24 together define a three-dimensional pant configuration having a waist opening 50 and a pair of leg openings 52. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52. The front region 22 includes the portion of the diaper 20 which, when worn, is positioned on the front of the wearer while the back region 24 includes the portion of the diaper which, when worn, is positioned on the back of the wearer. The crotch region 26 of the diaper 20 includes the portion of the diaper which, when worn, is positioned between the legs of the wearer and covers the lower torso of the wearer.

The absorbent chassis 32 is configured to contain and/or absorb any body exudates discharged from the wearer. For example, the absorbent chassis 32 can include a pair of elasticized containment flaps (not shown) which are configured to provide a barrier to the transverse flow of body exudates. The elasticized containment flaps define an unattached edge which assumes an upright, generally perpendicular configuration in at least the crotch region 26 of the diaper 20 to form a seal against the wearer's body. The containment flaps suitably include a stretchable/extensible casing that is both transversely and longitudinally stretchable/extensible. Suitable constructions and arrangements for the containment flaps are generally well known to those skilled in the art and are described in U.S. Pat. No. 4,704,116 issued Nov. 3, 1987 to Enloe, which is incorporated herein by reference. Alternatively, instead of containment flaps, absorbent gaskets (not shown) having a vertically or horizontally oriented superabsorbent core wrapped in a stretchable casing, with the casing forming a stem, can be attached to the inner surface 28 of the diaper 20 with the stem.

For reference, arrows 48 and 49 depicting the orientation of the longitudinal axis and the transverse axis, respectively, of the diaper 20 are illustrated in FIGS. 2–4.

In order for the diaper 20 to have all-over stretch, many components of the diaper 20 must be stretchable and attachment to non-stretchable components minimized. Thus, the diaper 20 includes a biaxially stretchable outer cover 40, a biaxially stretchable body side liner 42 which is connected to the outer cover 40 in a superposed relation, and a stretchable absorbent assembly 44 which is located between the outer cover 40 and the body side liner 42, as shown in FIGS. 2 and 3. The absorbent assembly 44 can either be biaxially stretchable, or longitudinally stretchable, i.e., stretchable along the longitudinal axis 48. When the absorbent assembly 44 is longitudinally stretchable and not transversely stretchable, it is bonded to the outer cover 40 and/or the body side liner 42 only at the longitudinal (front and back) ends of the absorbent assembly 44, not along the transverse sides of the absorbent assembly 44, as explained in more detail below. The biaxially stretchable materials provide superior fit and comfort due to the resulting diaper's 20 ability to stretch and equalize tensions in any direction in any part of the diaper 20. Furthermore, the total stretchability of the diaper 20 does not restrict a wearer's movements.

FIG. 2 shows the biaxially stretchable outer cover 40 of the diaper 20. More specifically, the outer cover 40 can stretch in both the longitudinal, or machine direction 48, and the transverse, or cross direction 49. The body side liner 42, shown in FIG. 3, is also biaxially stretchable, as mentioned. The outer cover 40 and the body side liner 42 can either be stretchable, or can be stretchable and retractable, thereby having elastomeric properties. Furthermore, the outer cover 40 and the body side liner 42 can have different degrees of stretchability and/or retractability through the use of a combination of various materials or a single material with various zones of stretchability and/or retractability.

Figure 5:
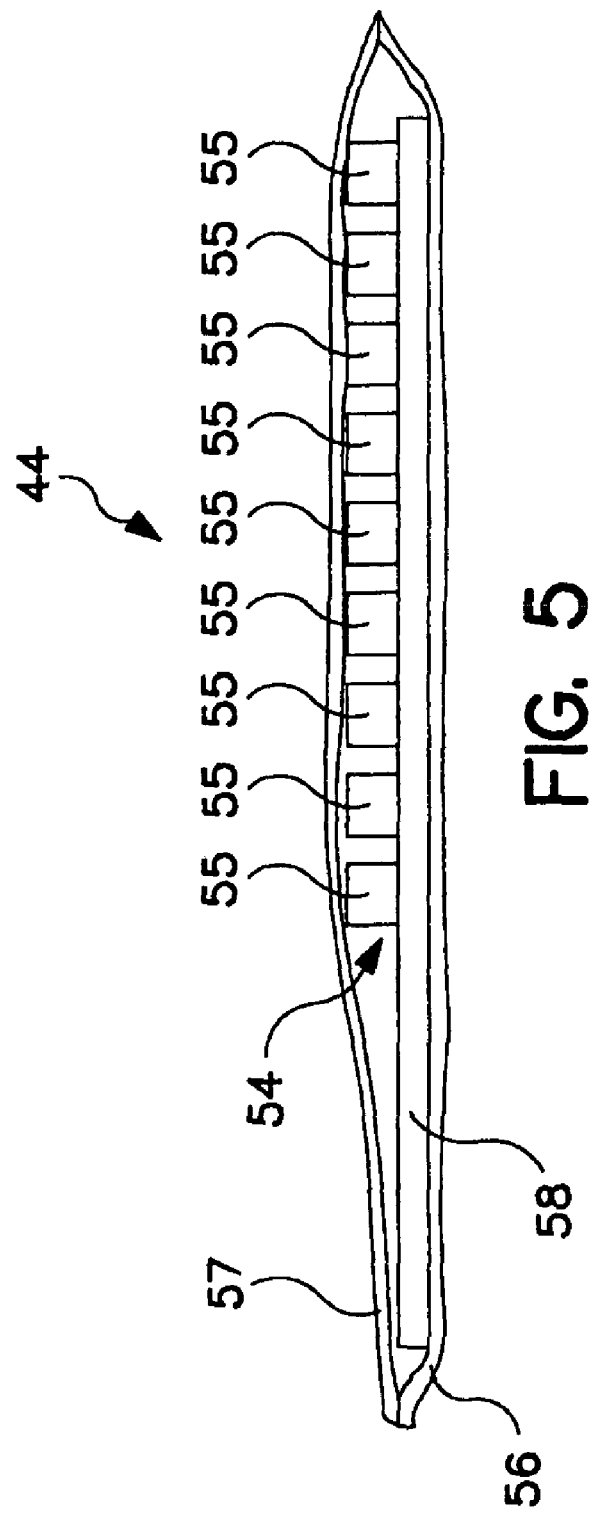
FIG. 5 is a cross-sectional view of the absorbent assembly of FIG. 4 taken along line 5—5.

The absorbent assembly 44 must be at least longitudinally stretchable/extensible, and may also be biaxially stretchable/extensible. In an embodiment having an absorbent assembly 44 that is longitudinally stretchable, but not transversely stretchable, the absorbent assembly 44 includes a segmented layer 54. More specifically, as shown in FIGS. 4 and 5, the absorbent assembly 44 includes a bottom carrier layer 56, a top carrier layer 57 (not shown in FIG. 4) which is connected to the bottom carrier layer 56 in a superposed relation, a continuous layer 58 which is bonded between the top carrier layer 57 and the bottom carrier layer 56, and the segmented layer 54 which is bonded either between the top carrier layer 57 and the continuous layer 58, as shown in FIG. 5, or between the bottom carrier layer 56 and the continuous layer 58. The segmented layer 54 includes a plurality of spaced apart segments 55.

One or both carrier layers 56, 57 extend beyond the absorbent region of the assembly to form front and/or back tails 60, 62. These tails 60, 62 are attached to the front and/or back waist edges 38, 39, respectively, of the body side liner 42 and/or the outer cover 40. As mentioned, when the absorbent assembly 44 is longitudinally stretchable and not transversely stretchable, the absorbent assembly 44 is bonded to the outer cover 40 and/or the body side liner 42 only at the longitudinal ends of the absorbent assembly 44, i.e., at the tails 60, 62, and is not bonded to the outer cover 40 and/or the body side liner 42 along the transverse edges of the absorbent assembly 44. The tails 60, 62 are extensions of the carrier layer, or layers 56, 57, and are transversely discontinuous, such that when bonded to the biaxially stretchable body side liner 42 and/or biaxially stretchable outer cover 40, the transverse stretch of the body side liner 42 and/or outer cover 40 is not hindered by the lack of transverse stretchability in the absorbent assembly.

The top and bottom carrier layers 57, 56, the continuous layer 58 and the segmented layers 54 are bonded together, either sonically or by any other suitable type of bonding. The top and bottom carrier layers 57, 56 include a stretchable or elasticized material that allows at least longitudinal extension. Alternatively, a biaxially stretchable material can be used to make the top and bottom carrier layers 57, 56, in which case tails 60, 62 would not be necessary and the carrier layers 57, 56 could be bonded about any portion within a perimeter of the carrier layers 57, 56. An example of suitable material for the top and bottom carrier layers 57, 56 is neck-stretched nonwoven material rotated 90 degrees so that the machine direction of the spunbond corresponds to the transverse axis of the diaper 20, thus imparting longitudinal stretch to the carrier layers 56, 57. Examples of suitable neckable materials include porous nonwoven materials such as, for example, spunbonded web, meltblown web or bonded carded web. If the neckable material is a web of meltblown fibers, it may include meltblown microfibers. The neckable material may be made of fiber forming polymers such as, for example, polyolefins. Exemplary polyolefins include one or more of polypropylene, polyethylene, ethylene copolymers, propylene copolymers, and butene copolymers. Useful polypropylenes include, for example, polypropylene available from the ExxonMobil Chemical Company under the trade designation Exxon 3445, and polypropylene available from Shell Chemical Company under the trade designation DX 5A09.

Alternatively, the neckable web may be a multilayer material having, for example, at least one layer of spunbonded web joined to at least one layer of meltblown web, bonded carded web or other suitable material. For example, neckable material may be a multilayer material having a first layer of spunbonded polypropylene having a basis weight from about 0.2 to about 8 ounces per square yard (osy) (about 6.8–270 grams/m$^2$, or gsm), a layer of meltblown polypropylene having a basis weight from about 0.2 to about 4 osy (6.8–135 gsm), and a second layer of spunbonded polypropylene having a basis weight of about 0.2 to about 8 osy (6.8–270 gsm).

Other examples of suitable materials for the top and bottom carrier layers 57, 56 include vertical extrusion stranded through air bonded carded webs (TABCW) and creped spunbond. One technique of creping is taught, for example, in U.S. Pat. No. 4,810,556, issued to Kobayashi et al., hereby incorporated by reference. Essentially, the creping process involves coating a nonwoven fabric with a lubricant and then pressing the coated fabric between a drive roll and a plate having a rough sandpaper-like surface. The nonwoven fabric is crinkled in a wavelike fashion in the direction of movement of the fabric by the frictional force caused by the pressing.

The continuous layer 58 of the absorbent assembly can act as a surge layer when located between the top carrier layer 57 and the segmented layer 54 for added absorbency, or as a spacer when located between the bottom carrier layer 56 and the segmented layer 54 for enhancing breathability. The continuous layer 58 includes a stretchable or elasticized absorbent material that allows at least longitudinal extension. The continuous layer 58 suitably includes a matrix of hydrophilic fibers, such as a web of cellulosic fluff, such as wood pulp fluff, mixed with particles of a high-absorbency material commonly known as superabsorbent material. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. An example of a suitable continuous layer 58 material is a co-form material including 50% Favor 880 superabsorbent material, 40% eucalyptus pulp, and 10% KRATON® elastomeric resin. KRATON® is a trade designation for products available from Shell Chemical Company.

The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area. Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

The segmented layer 54 of the absorbent assembly need not be stretchable because the longitudinal separation between individual segments does not inhibit longitudinal stretch of any other component in the absorbent assembly or in the diaper 20. The segmented layer 54 is primarily an absorbent layer, similar to the continuous layer 58, but with the need to stretch. An example of material suitable for the segmented layer 54 includes 50% Favor 880 superabsorbent material, 40% softwood pulp and 10% polymer microfibers. Alternatively, 80% superabsorbent material/tissue laminate, such as that manufactured by Gelok, or 30% superabsorbent material/70% fluff pulp composites may be satisfactory for the segmented layer 54.

The ratio of continuous layer 58 absorbent material to segmented layer 54 absorbent material may vary from 100:0 to 0:100. There are advantages to having absorbent material in both layers. The continuous layer 58 provides some degree of liquid wicking and has a uniform appearance, plus, the continuous layer 58 adds elastic tension to the system. In contrast, the segmented layer 54 has rapid liquid intake and does not add tension to the system, however, the segmented layer 54 has a non-uniform appearance and texture.

As mentioned previously, the absorbent assembly can, alternatively, be composed solely of a continuous absorbent material that has the ability to extend at least longitudinally. The continuous absorbent assembly 44 can be any structure which is generally compressible, conformable, non-irritating to the child's skin, capable of absorbing and retaining liquids and certain body wastes, and longitudinally stretchable.

If the continuous absorbent assembly stretches longitudinally and not transversely, then the continuous absorbent assembly is preferably shaped as shown in FIGS. 2 and 3 with tails 60, 62 along the front and back waist edges 38, 39 in order to avoid inhibiting the transverse stretch of the body side liner 42 and/or the outer cover 40. If, however, the continuous absorbent assembly is biaxially stretchable, then no tails are required and the absorbent assembly can have relatively straight edges along the front and back waist edges 38, 39.

The continuous absorbent assembly 44 can be manufactured in a wide variety of sizes and shapes, and from a wide variety of liquid absorbent materials commonly used in the art. In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable stretchable/extensible tissue wrap that maintains the integrity and/or shape of the absorbent assembly.

The continuous absorbent assembly 44, as well as the continuous layer 58 of the absorbent assembly, can be rendered stretchable by a number of different techniques, including the incorporation of elastic components, or attaching absorbent material, described above, to a pre-stretched elastomer and allowing the absorbent material and the elastomer to retract before assembling the absorbent assembly 44 within the diaper 20. Yet another technique includes pleating or corrugating the absorbent material, and finally another technique includes creping the absorbent material, as described above.

In addition to the absorbent assembly 44, the absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

Suitable materials for the biaxially stretchable outer cover 40 include biaxially stretchable material and biaxially elastic stretchable material. One example of a suitable outer cover material is a 0.3 osy polypropylene spunbond that is necked 60% in the transverse direction 49 and creped 60% in the longitudinal direction 48, laminated with 3 grams per square meter (gsm) Findley 2525A styrene-isoprene-styrene based adhesive to 8 gsm PEBAX® 2533 film with 20% TiO2 concentrate. The outer cover 40 can suitably be stretched, transversely and/or longitudinally, by at least 50% (to at least 150% of an initial (unstretched) width and/or length of the outer cover 40). More suitably, the outer cover 40 can be stretched, transversely and/or longitudinally, by at least 100% (to at least 200% of the unstretched width or length of the outer cover 40). Even more suitably, the outer cover 40 can be stretched, transversely and/or longitudinally, by at least 150% (to at least 250% of the unstretched width or length of the outer cover 40). Tension in the outer cover 40 at 50% extension is suitably between 50 and 1000 grams, more suitably between 100 and 600 grams, as measured on a 3 inch wide piece of the outer cover material.

The stretchable outer cover 40 desirably includes a material that is substantially liquid impermeable. The stretchable outer cover 40 can be a single layer of liquid impermeable material, but desirably includes a multi-layered laminate structure in which at least one of the layers is liquid impermeable. For instance, the stretchable outer cover 40 can include a liquid permeable outer layer and a liquid impermeable inner layer that are suitably joined together by a laminate adhesive (not shown) or thermal bonded attachment means. Suitable laminate adhesives, which can be applied continuously or intermittently as beads, a spray, parallel swirls, or the like, can be obtained from Ato-Findley Adhesives, Inc., of Wauwatosa, Wis., U.S.A., or from National Starch and Chemical Company, Bridgewater, N.J., U.S.A.

The liquid permeable outer layer can be any suitable material and desirably one that provides a generally cloth-like texture. One example of such a material is a thermoplastic nonwoven web, such as a spunbond thermoplastic nonwoven web made from a stretchable polymer and having a basis weight of about 1–100 grams per square meter (gsm), suitably about 5–50 gsm, more suitably 10–30 gsm. Suitable stretchable polymers for making the nonwoven web include certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Other stretchable polymers include very low density polyethylene (VLDPE), which is an ethylene-alpha olefin copolymer having a density less than 0.900 grams/cm$^3$, preferably about 0.870–0.890 grams/cm$^3$. Preferred VLDPE's are single-site catalyzed. Other stretchable polymers include random propylene-alpha olefin copolymers containing more than 10% by weight of a $C_2$ or $C_4$–$C_{12}$ comonomer, preferably about 15–85% by weight of the comonomer, with ethylene being a preferred comonomer.

The inner layer of the outer cover 40 can be both liquid and vapor impermeable, or can be liquid impermeable and vapor permeable. The inner layer is desirably manufactured from a thin (1–50 microns, suitably 5–25 microns, more suitably 10–20 microns) plastic film, although other stretchable liquid impermeable materials may also be used. The film can contain a blend of a thermoplastic polymer and a 30–70% by weight of a particulate inorganic filler, such as calcium carbonate. The film can be oriented at least uniaxially to cause void formation around the filler particles, resulting in breathability. Suitable stretchable polymers for making the film include stretchable olefin polymers, such as an olefinic copolymer of polyethylene. More specifically, other stretchable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E. I. du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.91 grams/cc, available from Dow Chemical Co. under the trade name AFFINITY®. The inner layer, or the liquid impermeable stretchable outer cover 40 when a single layer, prevents waste material from wetting articles, such as bedsheets and clothing, as well as the wearer and care giver.

Suitable materials for the stretchable outer cover 40 include a spunbonded laminate, a meltblown laminate, a spunbond-meltblown-spunbond laminate, or a stretch-bonded laminate (SBL) made using a stretchable polymer or blend thereof. A more specific example of a suitable liquid impermeable film for use as a liquid impermeable inner layer, or a single layer liquid impermeable stretchable outer cover 40, is a 0.02 millimeter polyethylene film commercially available from Huntsman Packaging of Newport News, Va., U.S.A. If the stretchable outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the stretchable outer cover 40. A suitable "breathable" material is composed of a microporous polymer film or a nonwoven fabric that has been coated or otherwise treated to impart a desired level of liquid impermeability. A suitable microporous film is a PMP-1 poly(methyl pentene) film material commercially available from Mitsui Toatsu Chemicals, Inc., Tokyo, Japan, or an XKO-8044 polyolefin film commercially available from 3M Company, Minneapolis, Minn.

Another example of a suitable material for the stretchable outer cover is a breathable elastic film/nonwoven laminate, described in U.S. Pat. No. 5,883,028, issued to Morman et al., herein incorporated by reference. Examples of materials having two-way stretchability and retractability are disclosed in U.S. Pat. No. 5,116,662 issued to Morman and U.S. Pat. No. 5,114,781 issued to Morman, both of which are hereby incorporated by reference. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The body side liner 42 is illustrated in FIG. 3 as overlying the stretchable outer cover 40 and absorbent assembly 44, and may but need not have the same dimensions as the stretchable outer cover 40. The body side liner 42 is desirably biaxially stretchable in order to be able to expand along with the biaxially stretchable outer cover 40. The body side liner 42 may be biaxially stretchable, or biaxially stretchable and retractable (i.e., elastic). The stretchable body side liner 42 is desirably compliant, soft feeling, and non-irritating to the child's skin. Further, the stretchable body side liner 42 can be less hydrophilic than the absorbent assembly 44, to present a relatively dry surface to the wearer and permit liquid to readily penetrate through its thickness.

The biaxially stretchable body side liner 42 can be manufactured from a wide selection of web materials, such as synthetic fibers (for example, polyester or polypropylene fibers), a combination of synthetic and natural fibers (examples of natural fibers including cotton fibers), porous foams, reticulated foams, apertured plastic films, or the like. The stretchable body side liner 42 can suitably be composed of a neck-stretched, spunbond web with KRATON® G strands, such as 0.4 osy (60% neck-stretched) polypropylene spunbond laminated to 0.4 osy strands of KRATON® MM G2760 with 12 strands per inch, which is stretched then allowed to retract. Other suitable materials may be extensible biaxial stretch materials such as neck stretched/creped spunbond.

The stretchable body side liner 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire stretchable body side liner 42 or can be selectively applied to particular sections of the stretchable body side liner, such as the medial section along the longitudinal centerline.

The diaper 20 includes a fastening system 78 operatively attached to the outer cover 40 along the transversely opposed side edges 36 just below the waist edges 38 and 39. The fastening system 78 can include side panels with tabs, straps, tearable seams, or similar devices, that can be fastened to the front region 22 of the outer cover 40 by suitable means, including adhesives or hook and loop fasteners.

To further enhance containment and/or absorption of body exudates, the diaper 20 can include waist elastic members 80 and/or leg elastic members 82, as are known to those skilled in the art (FIG. 1). The waist elastic members 80 can be operatively joined to the stretchable outer cover 40 and/or the stretchable body side liner 42, and can extend over part or all of the waist edges 38, 39. The leg elastic members 82 are desirably operatively joined to the stretchable outer cover 40 and/or the stretchable body side liner 42 longitudinally along the opposite side edges 36 and positioned in the crotch region 26 of the diaper 20.

The waist elastic members 80 and the leg elastic members 82 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 80 and/or the leg elastic members 82 include a plurality of dry-spun coalesced multifilament spandex elastomeric threads sold under the trade name LYCRA® and available from E. I. du Pont de Nemours and Company, Wilmington, Del., U.S.A. In another particular embodiment, for example, the waist elastic members 80 and/or the leg elastic members 82 include Findley HX 2695-01 adhesive laminated to two facings of 0.6 osy bicomponent polypropylene/polyethylene spunbond. Alternatively, up to about six strands of 310 decitex LYCRA® may be also laminated at 250% elongation between the spunbond facings in addition to the Findley adhesive.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A disposable absorbent garment, comprising:
a chassis having a biaxially stretchable body side liner,
a stretchable absorbent assembly including a continuous layer of absorbent material positioned adjacent at least one stretchable carrier layer, and
a biaxially stretchable outer cover;
the chassis defining a pair of leg openings and a waist opening;
the absorbent assembly having a segmented layer bonded to the continuous layer with at least one tail at a first longitudinal end of the absorbent assembly and at least one tail at a second longitudinal end of the absorbent assembly;
wherein the absorbent assembly is positioned between the body side liner and the outer cover and at least one of the tails at the first and second longitudinal ends of the absorbent assembly is bonded to at least one of the body side liner and the outer cover.

2. The absorbent garment of claim 1, wherein the stretchable absorbent assembly is longitudinally stretchable.

3. The absorbent garment of claim 1, wherein the stretchable outer cover comprises a biaxially elastic stretchable material.

4. The absorbent garment of claim 1, wherein the absorbent assembly comprises a corrugated material.

5. The absorbent garment of claim 1, wherein the absorbent assembly comprises a creped material.

6. A disposable absorbent garment, comprising:
a chassis having a biaxially stretchable body side liner,
a longitudinally stretchable absorbent assembly, and
a biaxially stretchable outer cover;
the chassis defining a pair of leg openings and a waist opening;
the absorbent assembly having at least one stretchable carrier layer, a continuous layer adjacent the at least one carrier layer, and a segmented layer bonded to the continuous layer with at least one tail at a first longitudinal end of the absorbent assembly and at least one tail at a second longitudinal end of the absorbent assembly;
wherein the absorbent assembly is positioned between the body side liner and the outer cover and the tails at the first and second longitudinal ends of the absorbent assembly are bonded to at least one of the body side liner and the outer cover.

7. The absorbent garment of claim 6, wherein the stretchable outer cover comprises a biaxially elastic stretchable material.

8. The absorbent garment of claim 6, wherein the at least one tail along at least one longitudinal end is an extension of the at least one carrier layer.

9. The absorbent garment of claim 6, wherein the at least one carrier layer comprises a material having longitudinal stretch.

10. The absorbent garment of claim 6, wherein the at least one carrier layer comprises a material having longitudinal stretch and retractability.

11. The absorbent garment of claim 6, wherein the at least one carrier layer comprises a neck stretched spunbond material.

12. The absorbent garment of claim 6, wherein the at least one carrier layer comprises a vertical extrusion stranded through air bonded carded web.

13. The absorbent garment of claim 6, wherein the at least one carrier layer comprises a creped spunbond.

14. The absorbent garment of claim 6, wherein the continuous layer comprises a material having longitudinal stretch.

15. The absorbent garment of claim 6, wherein the continuous layer comprises a material having longitudinal stretch and retractability.

16. The absorbent garment of claim 6, wherein the continuous layer comprises a superabsorbent material.

17. The absorbent garment of claim 6, wherein the segmented layer comprises a superabsorbent material.

18. A biaxially stretchable disposable absorbent garment, comprising:
a chassis having a biaxially stretchable body side liner, a stretchable absorbent assembly including a continuous layer of absorbent material positioned adjacent at least one stretchable carrier layer, and a stretchable outer cover, the chassis defining a pair of leg openings and a waist opening; and
wherein the absorbent assembly comprises a top carrier layer, a bottom carrier layer, a continuous layer between the top and bottom carrier layers, and a segmented layer bonded to the continuous layer; and
wherein the continuous layer comprises a superabsorbent material.

* * * * *